(12) United States Patent
Choubey et al.

(10) Patent No.: US 9,579,427 B2
(45) Date of Patent: Feb. 28, 2017

(54) THIN-FILM COMPOSITE RETRIEVABLE ENDOVASCULAR DEVICES AND METHOD OF USE

(71) Applicant: Cordis Corporation, Fremont, CA (US)

(72) Inventors: Animesh Choubey, Fremont, CA (US); Ramesh Marrey, Pleasanton, CA (US)

(73) Assignee: CORDIS CORPORATION, Milpitas, CA (US)

( * ) Notice: Subject to any disclaimer, the term of this patent is extended or adjusted under 35 U.S.C. 154(b) by 138 days.

(21) Appl. No.: 14/318,610

(22) Filed: Jun. 28, 2014

(65) Prior Publication Data

US 2014/0358213 A1    Dec. 4, 2014

(51) Int. Cl.
*A61F 2/07* (2013.01)
*A61L 31/14* (2006.01)
(Continued)

(52) U.S. Cl.
CPC ............ *A61L 31/146* (2013.01); *A61F 2/01* (2013.01); *A61F 2/91* (2013.01); *A61F 2/95* (2013.01); *A61F 2/962* (2013.01); *A61L 31/022* (2013.01); *A61L 31/048* (2013.01); *A61F 2002/018* (2013.01); *A61F 2002/9528* (2013.01);
(Continued)

(58) Field of Classification Search
CPC ...... A61F 2/91; A61F 2/95; A61F 2/01; A61F 2/962; A61F 2210/0076; A61F 2002/018; A61F 2250/0039; A61F 2250/0014; A61F 2250/0068; A61F 2250/0059; A61F 2002/9528; A61F 2250/0067;
(Continued)

(56) References Cited

U.S. PATENT DOCUMENTS 4,733,665 A    3/1988 Palmaz
5,091,205 A    2/1992 Fan
(Continued)

FOREIGN PATENT DOCUMENTS

EP    2665510 A2    11/2013
WO    2004032805 A1    4/2004
(Continued)

OTHER PUBLICATIONS

Gupta, Vikas et al., "Nitinol Thin film Three-Dimensional Devices—Fabrication and Applications", TiNi Alloy Company, Sep. 2003.
(Continued)

*Primary Examiner* — Julian W Woo

(57) ABSTRACT

Various embodiments for a composite endovascular device (and variations thereof) that include an inner polymer structure and an outer thin-film shape memory structure. The inner polymer structure extends from a distal end to a proximal end along a longitudinal axis. The outer thin-film shape-memory structure has an inner thin-film surface coupled to the outer surface of the inner polymer structure from the distal end to the proximal end with a retrieval member at the proximal end to allow for the prosthesis to be retrieved after placement in a body vessel. The inner polymeric structure can be blended with a suitable bio-active agent or the agent can be loaded into the pores. The device can be permanent or temporary by virtue of being retrievable.

18 Claims, 7 Drawing Sheets

(51) Int. Cl.
*A61L 31/02* (2006.01)
*A61F 2/95* (2013.01)
*A61L 31/04* (2006.01)
*A61F 2/91* (2013.01)
*A61F 2/962* (2013.01)
*A61F 2/01* (2006.01)

(52) U.S. Cl.
CPC .............. *A61F 2210/0076* (2013.01); *A61F 2250/0014* (2013.01); *A61F 2250/0039* (2013.01); *A61F 2250/0059* (2013.01); *A61F 2250/0067* (2013.01); *A61F 2250/0068* (2013.01); *A61L 2400/16* (2013.01)

(58) Field of Classification Search
CPC .... A61L 31/048; A61L 31/022; A61L 31/146; A61L 2400/16
See application file for complete search history.

(56) References Cited

U.S. PATENT DOCUMENTS

| | | | |
|---|---|---|---|
| 5,474,563 A * | 12/1995 | Myler | A61F 2/91 606/108 |
| 5,512,055 A | 4/1996 | Domb et al. | |
| 5,755,770 A | 5/1998 | Ravenscroft | |
| 5,795,318 A | 8/1998 | Wang et al. | |
| 5,824,046 A | 10/1998 | Smith et al. | |
| 6,616,650 B1 | 9/2003 | Rowe | |
| 7,163,555 B2 * | 1/2007 | Dinh | A61F 2/91 623/1.18 |
| 7,166,100 B2 | 1/2007 | Jordan et al. | |
| 8,460,333 B2 | 6/2013 | Boyle et al. | |
| 2002/0062133 A1 | 5/2002 | Gilson et al. | |
| 2003/0028246 A1 | 2/2003 | Palmaz et al. | |
| 2009/0105737 A1 | 4/2009 | Fulkerson et al. | |
| 2009/0125053 A1 | 5/2009 | Ferrera et al. | |
| 2009/0220571 A1 | 9/2009 | Eaton et al. | |
| 2010/0312264 A1 | 12/2010 | O'Brien et al. | |
| 2012/0101560 A1 | 4/2012 | Kluck | |
| 2014/0025005 A1 | 1/2014 | Stankus et al. | |

FOREIGN PATENT DOCUMENTS

| | | |
|---|---|---|
| WO | 2006044632 A2 | 4/2006 |
| WO | 2010096208 A2 | 8/2010 |
| WO | 2011082319 A1 | 7/2011 |

OTHER PUBLICATIONS

Abizaid A., et al., "Advances in Interventional Cardiology," Circulation: Cardiovascular Interventions, 2010, vol. 3, pp. 384-393.
International Seach Report and Written Opinion for PCT Application No. PCT/US2015/036122 mailed on Oct. 5, 2015.

* cited by examiner

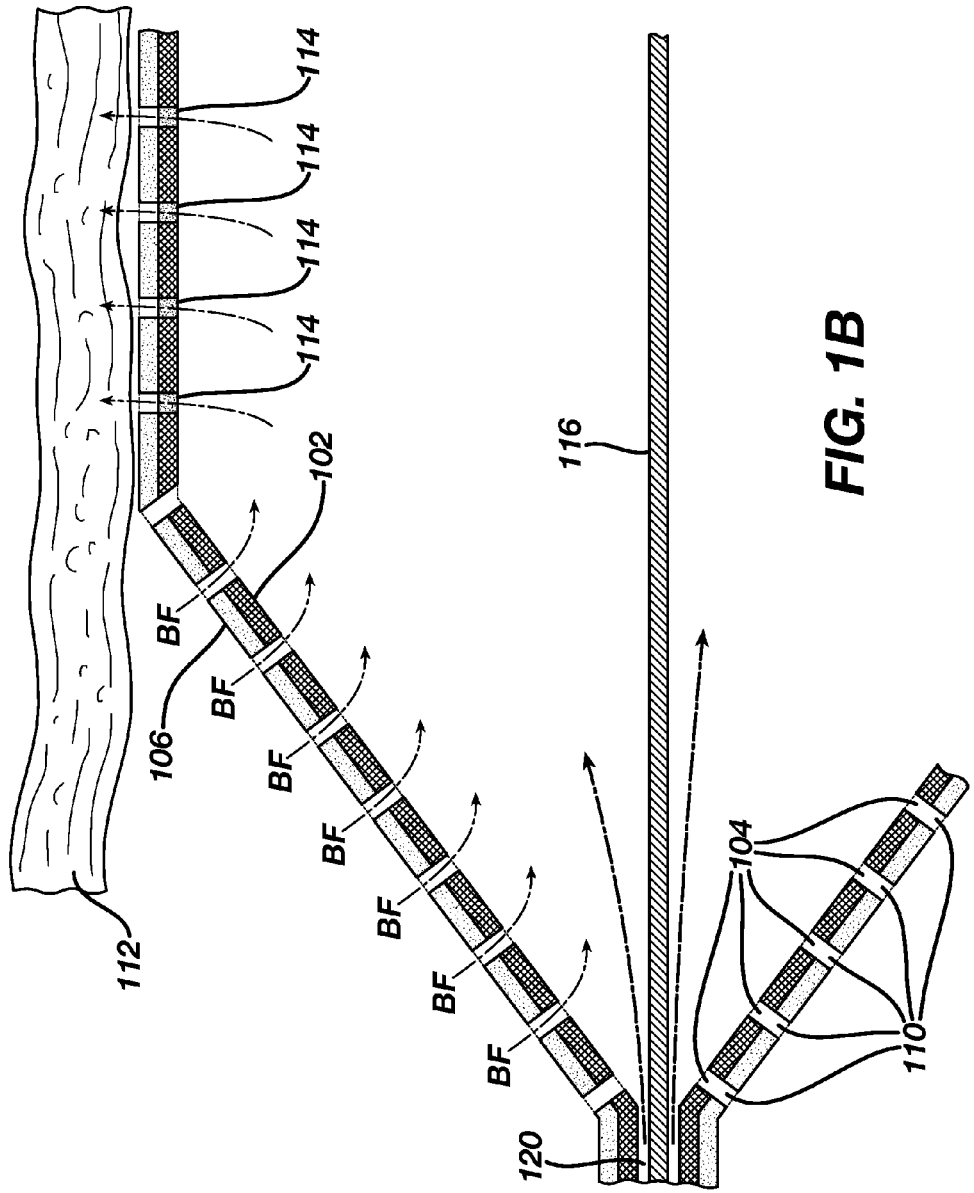

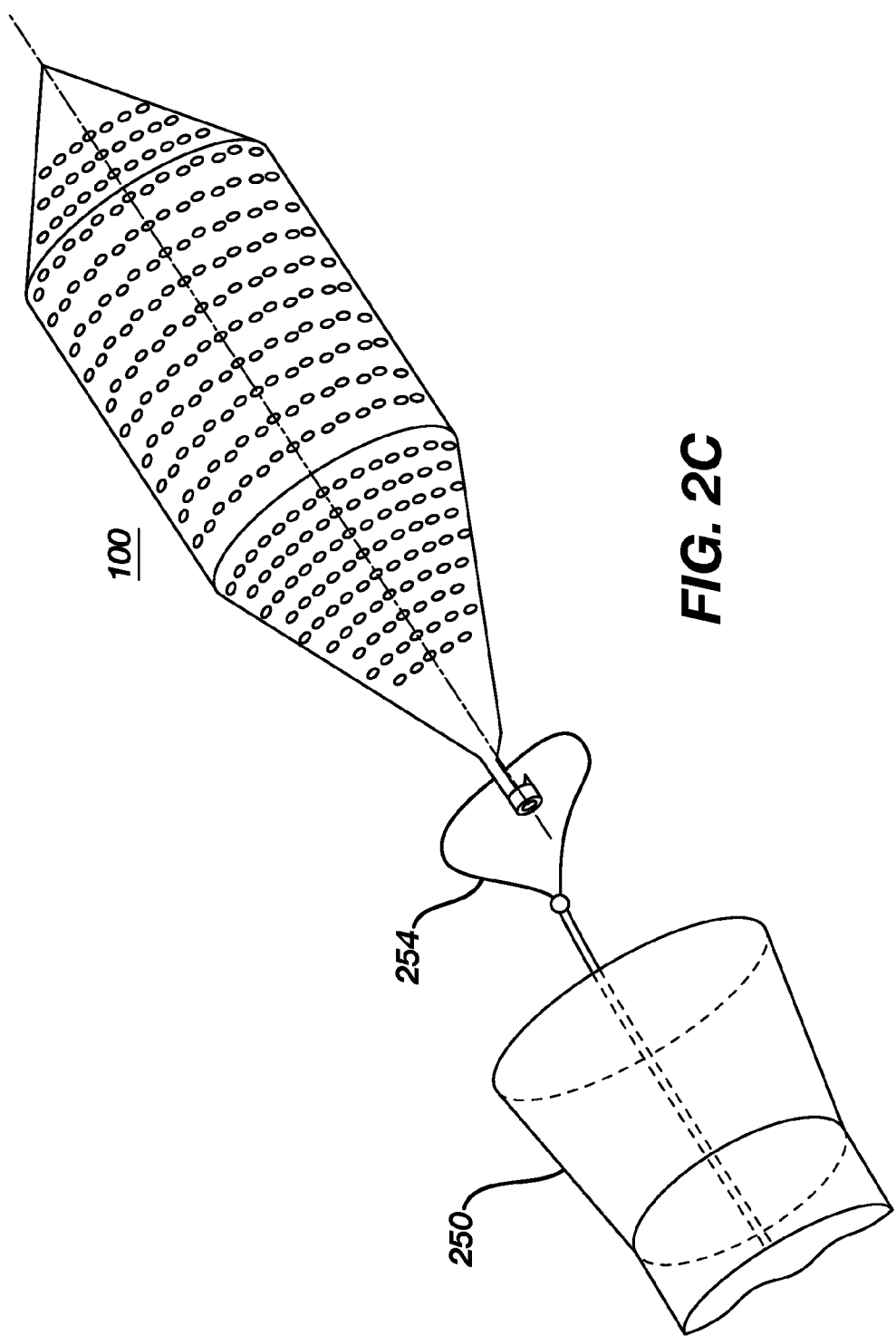

THIN-FILM COMPOSITE RETRIEVABLE ENDOVASCULAR DEVICES AND METHOD OF USE

BACKGROUND

It is well known to employ various intravascular endoprostheses delivered percutaneously for the treatment of diseases of various body vessels. These types of endoprosthesis are commonly referred to as stents. A stent is a generally formed longitudinal tubular device of biocompatible material, such as stainless steel, cobalt-chromium, nitinol or biodegradable materials, having holes or slots cut therein so they can be radially expanded, by a balloon catheter or the like, or alternately self-expanded within the vessel. Stents are useful in the treatment of stenosis, strictures or aneurysms in body vessels such as blood vessels. These devices are implanted within the vessel to reinforce collapsing, partially occluded, weakened or abnormally dilated sections of a vessel. Stents are typically employed after angioplasty of a blood vessel to prevent restenosis of the diseased vessel. While stents are most notably used in blood vessels, stents may also be implanted in other body vessels such as the urogenital tract and bile duct.

Stents generally include an open flexible configuration. This configuration allows the stent to be inserted through curved vessels. Furthermore, the stent configuration allows the stent to be configured in a radially compressed state for intraluminal catheter implantation. Once properly positioned adjacent the damaged vessel, the stent is radially expanded so as to support and reinforce the vessel. Radial expansion of the stent can be accomplished by inflation of a balloon attached to the catheter, or alternatively using self-expanding materials such as nitinol within the stent. Examples of various stent constructions are shown in U.S. Pat. No. 4,733,665 filed by Palmaz on Nov. 7, 1985, which is hereby incorporated herein by reference.

A balloon angioplasty can be used in place or as an adjunct to a stent implant. As is well known, a balloon is deployed in a narrowed blood vessel and expanded to open up the narrowed vessel. Once the vessel has regained sufficient flow, the balloon is withdrawn.

With either of these techniques, restenosis may develop subsequent to the procedure in about half of the patient receiving a stent. Restenosis is believed to be even higher for angioplasty. To reduce the rate of restenosis, drug eluting stents are provided, which has been shown to be superior to bare metal stents in reducing the restenosis. However, thrombosis for drug eluting stent has been shown to be problem over time, believed to be as much as five years or longer. Additionally, the polymer carrier for the drug in such drug eluting stent is believed to be a source of the inflammatory response or local toxicity by the body vessel.

SUMMARY OF THE DISCLOSURE

We have devised a heretofore novel composite endovascular device that overcomes or even eliminates most of the shortcomings of the existing stent graft device. In particular, we have devised an endovascular prosthesis that includes an inner polymer structure and an outer thin-film shape memory structure. The inner polymer structure extends from a distal end to a proximal end along a longitudinal axis. The inner polymer structure has an inner surface facing the longitudinal axis with a first plurality of pores with each pore extending from the inner surface to an outer surface of the polymer structure. The outer thin-film shape-memory structure has an inner thin-film surface coupled to the outer surface of the inner polymer structure from the distal end to the proximal end with a retrieval member at the proximal end to allow for the prosthesis to be retrieved after placement in a body vessel. The outer thin-film shape-memory structure is configured with a second plurality of pores with each pore extending from the inner thin-film surface to an outer thin-film surface so that fluid communication is provided from the inside of the inner polymer structure to the body vessel.

By virtue of this composite device, we have devised a method of using the device that can be achieved by: inserting the prosthetic mounted on a delivery catheter into a blood vessel proximate a location with arterial deposits on an inner wall of the blood vessel; deploying the prosthetic in the blood vessel proximate the location with arterial deposits; removing the delivery catheter from the blood vessel; and retrieving the prosthetic after a time period subsequent to the deploying step.

Alternative embodiments of the invention can be achieved when utilized with other features noted hereafter: one of the first and second pluralities of pores includes a proportion of the pores filled with a bio-active material for elution directly into the body vessel; the proportion of pores with bio-active materials includes 80% of the plurality of pores; the inner polymer structure is connected to a guidewire lumen that extends through the proximal end to the distal end to allow for insertion of a guide wire; the guidewire lumen is disposed between the inner polymer structure and an inflation lumen; the inner polymer structure includes a polyethylene material; the inner polymer structure includes a polymer blended with bio-active agents configured to timed release; the inner polymer structure includes a biodegradable polymer; the outer thin-film balloon includes a biocompatible metal; the biocompatible metal includes a thin-film of nitinol; the biocompatible metal includes a thin-film of cobalt chromium; the outer thin-film structure includes a first frustoconic joining a cylinder and terminating in a second frustoconic to define the overall outer shape of the prosthesis; each of the plurality of pores is disposed in a radial direction with respect to the longitudinal axis; at least one of the first and second plurality of pores disposed on the first and second frustoconic allows for a portion of blood in the body vessel to flow through the pores on the first and second frustoconic; the retrieval member includes a hook configured to engage with retrieval snare of a retrieval catheter; the retrieval member includes a radial member configured to engage with retrieval claws of a retrieval catheter; the first plurality of pores of the inner polymer structure are aligned with respective second plurality of pores of the thin-film outer thin-film structure.

These and other embodiments, features and advantages will become apparent to those skilled in the art when taken with reference to the following more detailed description of the exemplary embodiments of the invention in conjunction with the accompanying drawings that are first briefly described.

BRIEF DESCRIPTION OF DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements), in which:

FIG. 1B is a close-up sectional view of a portion of FIG. 1A;

FIG. 2C illustrates a perspective view of another retrieval system;

MODES OF CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. The term "proximal" indicates the location of a component closest to the operator of the subject device and "distal" indicates the location of a component furthest from the operator and where the location of the operator is not apparent, the distal end is opposite to the proximal end. In addition, as used herein, the terms "patient," "host," "user," and "subject" refer to any human or animal subject and are not intended to limit the systems or methods to human use, although use of the subject invention in a human patient represents a preferred embodiment.

Figure 1A:
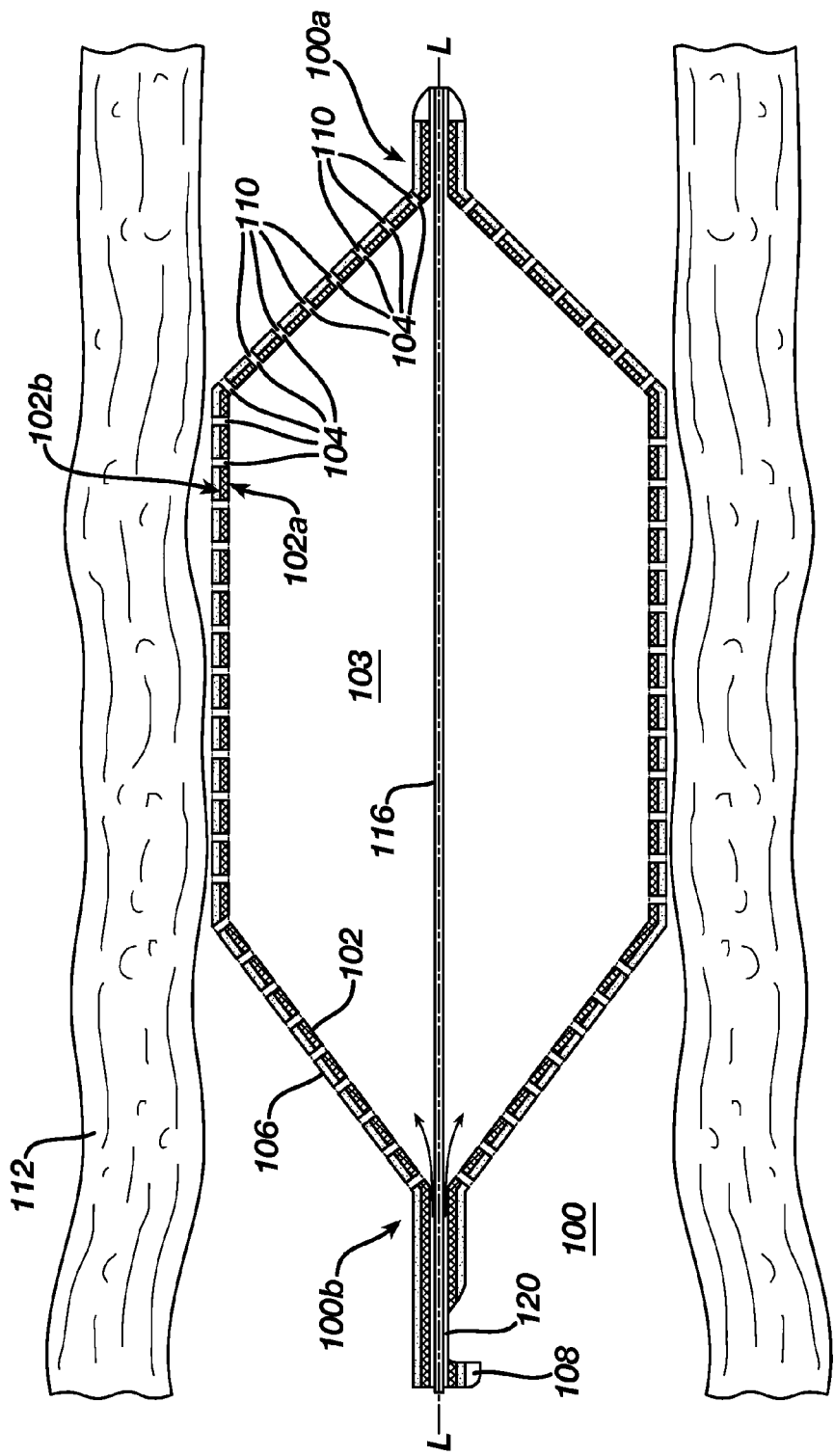
FIG. 1A is a sectional view of one embodiment of the composite endovascular prosthetic device inside a body vessel.

Referring now to the drawings wherein like numerals indicate the same element throughout the views, there is shown in FIG. 1A an endovascular prosthesis 100 composed mainly of two components: (1) an inner polymer structure 102 and (2) an outer thin-film structure 106 that extends from a distal end 100a to a proximal end 100b along a longitudinal axis L-L. The inner polymer structure 102 has an inner surface 102a facing the longitudinal axis L-L with a first plurality of pores 104 provided for the inner polymer structure 102. It is noted that each pore extends from the inner surface 102a of inner polymer structure 102 to an outer surface 102b of the polymer inner polymer structure 102. The outer thin-film structure 106 has an inner thin-film surface 106a coupled to the outer surface 102b of the inner polymer structure 102. Like the inner polymer structure 102, the outer thin-film structure 106 extends from the distal end 100a to the proximal end 100b.

Both inner and outer structures 102 and 106 are unitary with each other so that both components are treated as a single member; that is, one could consider that both structures function together under certain conditions like a balloon, a stent or a blood filter.

To allow for retrieval of device 100 once placed into a body vessel 112, a retrieval member 108 is provided at the proximal end to allow for the prosthesis 100 to be retrieved by a retrieval catheter 250. Further, the outer thin-film structure 106 is also configured with a second plurality of pores 110. Each pore 110 extends from the inner thin-film surface 106a to an outer thin-film surface 106b so that fluid communication BF of the body vessel 112 is provided from the inside 103 of the inner polymer structure 102 to the body vessel 112. Specifically, the first plurality of pores 104 of the inner polymer structure 102 is aligned with respective second plurality of pores 110 of the thin-film outer structure 106.

To take advantage of the blood flow BF into and out of the pores 104 and 110, one of the first and second plurality of pores 104, 110 has a number of the pores (i.e., a proportion of the total number of pores) filled with a bio-active material 114 for elution directly into the body vessel 112. In one embodiment, the number of pores loaded with bio-active agents can be from about 20% to 80% of the total number of pores. The pores 104 of the inner polymer structure 102 may be aligned with corresponding pores 110 in the outer thin-film structure. The bio-active agent 114 can be disposed in one of the pores 104, 110 or in both pores. In another embodiment, none of the pores are filled or loaded with bio-active agents. Rather, timed-release bio-active agents are combined with the polymer inner polymer structure 102 such that the bioactive agent elutes out of the polymer inner polymer structure 102 into the pores 104, 110 for delivery into the body vessel 112. It is believed that one of the advantages of the invention is due to the thin-film outer thin-film structure 106 configured to physically contact the soft tissue of the body vessel 112. Consequently, blood flow BF tends to force the bio-active agent to be impinged directly into the tissue, shown here in FIG. 1B.

In FIG. 1B, it can be seen that the prosthesis 100 (via the inner structure 102) is connected to a guidewire lumen 116 that extends through the proximal end 100b of the prosthesis 100 to the distal end 100b to allow for insertion of a guide wire 118. As is known in the art, an inflation lumen 120 is provided for inflation of the inner and outer structures (102 and 106) with saline or additional bioactive agents other than that provided with agent 114. It is noted here that the inner polymer structure 102 can be formed from a suitable polymer, such as, for example, polyethylene, PTFE, ePTFE, Dacron, PET (polyester), Fluoro-polymers such as PTFE and FEP, spun PTFE, HDPE, and combinations thereof The inner polymer structure 102 can be formed from biodegradable polymers such as polylactic acid (i.e., PLA), polyglycolic acid (i.e., PGA), polydioxanone (i.e., PDS), polyhydroxybutyrate (i.e., PHB), polyhydroxyvalerate (i.e., PHV), and copolymers or a combination of PHB and PHV (available commercially as Biopol®), polycaprolactone (available as Capronor®), polyanhydrides (aliphatic polyanhydrides in the back bone or side chains or aromatic polyanhydrides with benzene in the side chain), polyorthoesters, polyaminoacids (e.g., poly-L-lysine, polyglutamic acid), pseudopolyaminoacids (e.g., with back bone of polyaminoacids altered), polycyanocrylates, or polyphosphazenes. As used herein, the term "bio-resorbable" includes a suitable biocompatible material, mixture of materials or partial components of materials being degraded into other generally non-toxic materials by an agent present in biological tissue (i.e., being bio-degradable via a suitable mechanism, such as, for example, hydrolysis) or being removed by cellular activity (i.e., bioresorption, bioabsorption, or bioresorbable), by bulk or surface degradation (i.e., bioerosion such as, for example, by utilizing a water insoluble polymer that is soluble in water upon contact with biological tissue or fluid), or a combination of one or more of the bio-degradable, bio-erodable, or bio-resorbable material noted above.

Referring to FIG. 1B, the outer thin-film structure 110 can be made from a biocompatible metal or pseudometals, such as, for example, nitinol, cobalt-chromium, magnesium, copper and the like. The prosthesis 100 may be provided with different shapes such as for example, an elongated tubular member (FIG. 1C) or one with a cylinder CYL joined at the ends of the cylinder with respective truncated cones F1 and F2 (i.e., frustoconical) in FIG. 1A. The pores 104, 110 can be aligned in various orientations. It is preferred that the pores 104 and 110 on the cylindrical portion CYL be aligned radially with respect to the longitudinal axis L-L such that the pores are aligned with an orthogonal plane with respect to axis L-L. The orientation of the pores 104, 110 on the first and second truncated cones F1 and F2 allow blood flow to be maintained through the blood vessel 112. In this regard, prosthetic 100 has characteristics of a blood filter while at the same time maintaining the patency of the vessel 112 that has been partially occluded by plaques 113 deposited on the inner surface 112a of the vessel 112 (FIG. 1C).

Figure 1C:
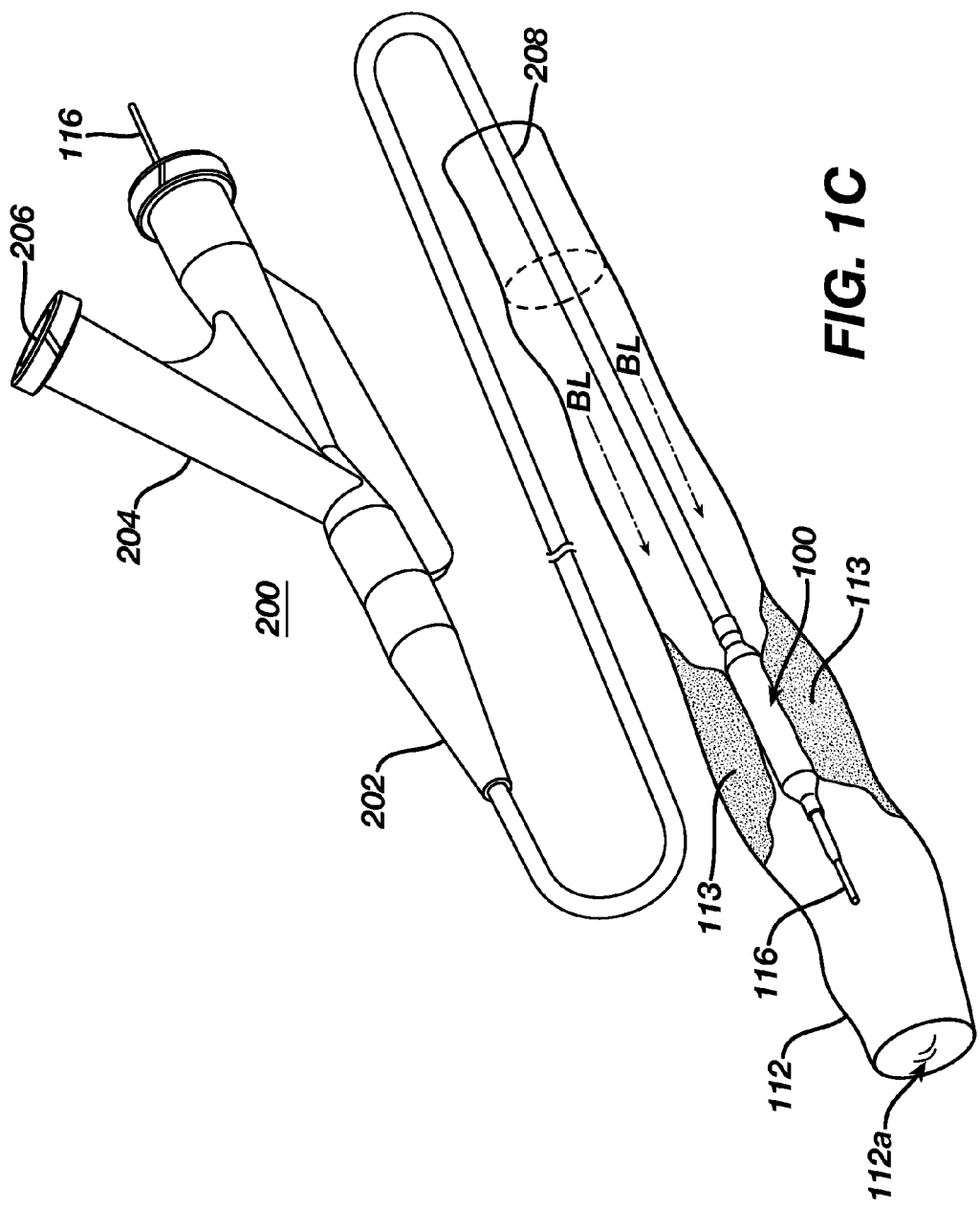
FIG. 1C is a perspective view of a system to deliver or retrieve the composite device with the composite device being shown proximate a narrowed body vessel.

In FIG. 1C, an exemplary delivery system 200 is shown with catheter boss 202, hub 204, port 206 with for delivery of saline or bio-active agents, catheter 208 with guide wire 116 for insertion of the device 100 inside a narrowed vessel 112 with inner surface 112a having plaques or deposits 113.

While the device can be left inside the body vessel permanently, under certain circumstances, a physician may desire to remove the device from the body vessel. In such cases, the device is provided with a retrieval member in the form of a hook 108 that can be coupled to a snare 254 of a retrieval catheter 250.

Instead of a retrieval hook, radial member 108' can be provided instead of the hook 108. The radial retrieval wheel 108' is configured to engage with retrieval claws 252 of the retrieval catheter 250.

Figure 3:
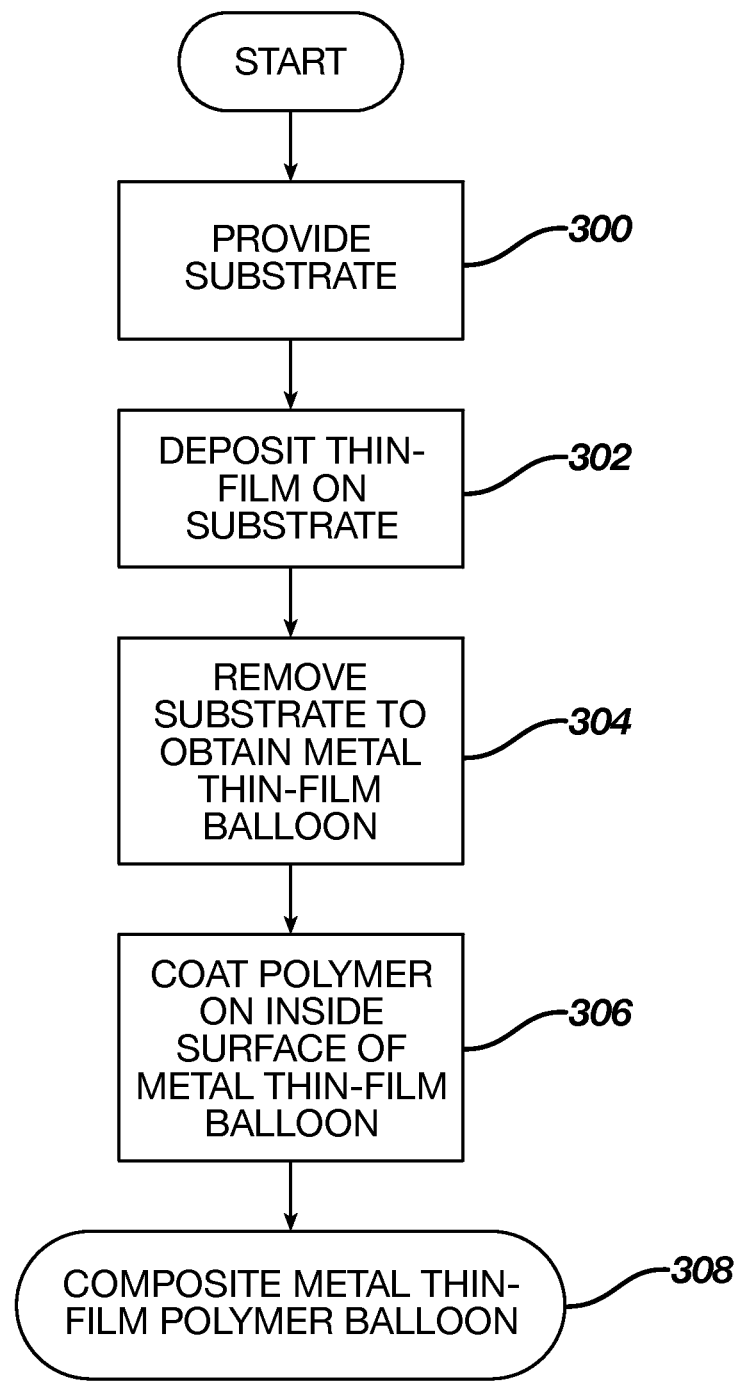
FIG. 3 illustrates the high level steps to make one embodiment of the device.

With reference to FIG. 3, the thin-film outer structure 106 is preferably formed by depositing (e.g., chemical or physical means) nitinol onto a substrate at step 302. Briefly, chemical deposition can be by plating, chemical solution deposition, spin coating, chemical vapor deposition, plasma enhanced vapor deposition, or atomic layer deposition. Physical deposition for thin film manufacturing can be by thermal evaporator, laser deposition, cathodic arc deposition, sputtering, vapor deposition, ion-beam assisted evaporative deposition or electrospray deposition. With any of these techniques, a sacrificial substrate (e.g., a cylindrical form of copper or a polymer) can be provided for thin-film material deposition and then removed at step 304 after the material deposition of step 302.

The substrate may have a dimensional configuration suitable for the intended use in the body. For example, the substrate may take the shape of two frustoconical forms joined to respective ends of a cylindrical substrate. Alternatively, the substrate may take the shape of an elongated balloon (FIG. 1C).

In yet another variation, a substrate can be formed via 3-D printing to a customized configuration for the metal (or pseudo-metal) deposition to achieve the thin-film outer structure 106. As used herein, the term "thin-film" indicates a structural material with a thickness from about 500 Angstroms to about 50 microns of metal (or pseudometals).

In order to form the pores 110 in the thin-film, the sacrificial material can be formed as three-dimensional structure (e.g., cylindrical structure) so that when the sacrificial material is removed, this leaves behind voids in the form of pores extending through the thin-film structure 106. After the thin-film outer structure is formed in step 302, it can be annealed or crystallized at high temperature. The sacrificial layer can be removed at step 304 by chemical etching, either before or after the annealing process.

In yet a further variation of the manufacturing technique of the thin-film outer structure, multiple layers of a metal (e.g., nitinol) are deposited on a generally planar sacrificial layer of a substrate then a layer of sacrificial material (e.g., chromium) is deposited on a portion of the thin-film layer to define a three-dimensional form for each pore. Thereafter, another layer of thin-film is further deposited over the prior thin-film layer and the sacrificial layer. This sequence can be repeated as needed. Thereafter, the sacrificial layer is removed including the layer contiguous to the substrate and the sacrificial layer that extends through the thin-film to define each of the pores. At this point the thin-film is in the form of a planar structure. To form a three dimensional structure such as a cone or cylinder, the planar thin-film structure is rolled onto a close fitting mandrel until the ends of the thin-film planar sheet abut each other to form seam. The seam can be joined together (e.g., welding with laser with inert gas, resistance welding under Argon, halogen soldering, brazing or ultrasonic soldering) to form a unitary structure in the form shown here in FIGS. 1A and 1C. Details of various techniques are shown and described in "NITINOL THIN FILM THREE-DIMENSIONAL DEVICES—FABRICATION AND APPLICATIONS" by Gupta et al., published by the TiNi Alloy Company, 2003 and U.S. Pat. No. 8,460,333, which are incorporated by reference as if set forth herein their entireties in this application.

Referring back to FIG. 3, the thin-film outer structure 106 formed at step 304 is then coated or dipped on its internal surface with a polymeric material blended with suitable bio-active agents. In the coating of the internal polymer layer, the polymer layer will tend to extrude through the pores formed on the outer thin-film structure. Alternatively, pores can be formed through the polymer inner structure via mechanical punching or by laser cutting through the existing pores formed on the outer thin-film structure. In the preferred embodiments, the pore can have any shape or a combination of shapes (including that of a circle) with a diameter from about 1 nm (nanometer) to about 300 micrometers (or microns). In another embodiment, the area defined by the pore, irrespective of its shape, can be from about 4 nanometer squared to about 10 micron squared. Regardless of whether the drug is loaded into the pores or blended with the inner polymer structure, the elution rate should be sufficient for therapeutic effects on the patient. The pores may be configured such that the pores proximate the distal and proximal ends of the device 100 are larger than the pores proximate the center of the device 100.

By virtue of the device, a method of use of the device can be achieved by providing the prosthetic as described earlier. With reference to FIG. 1C, the prosthetic is then mounted on the delivery catheter 200 and inserted into a blood vessel 112 to a location that may have excessive arterial deposits 113 disposed on an inner wall 112a of the blood vessel 112. Once at the desired location in the body vessel 112, the prosthetic can be deployed in the conventional manner (pulling back the outer sheath to allow the prosthetic to expand or using a pusher to push the prosthetic out of the delivery catheter).

Figure 2A:
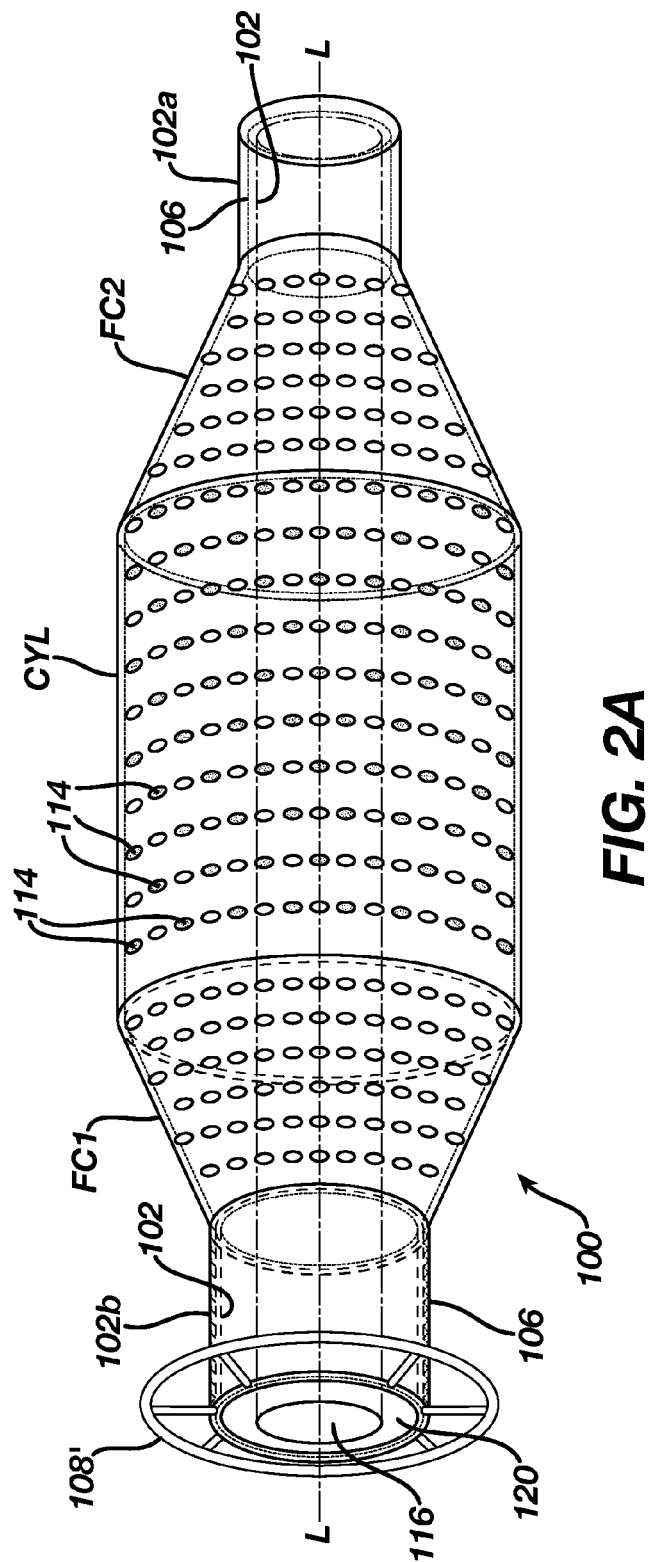
FIG. 2A illustrates in perspective another embodiment of the device.
Figure 2B:
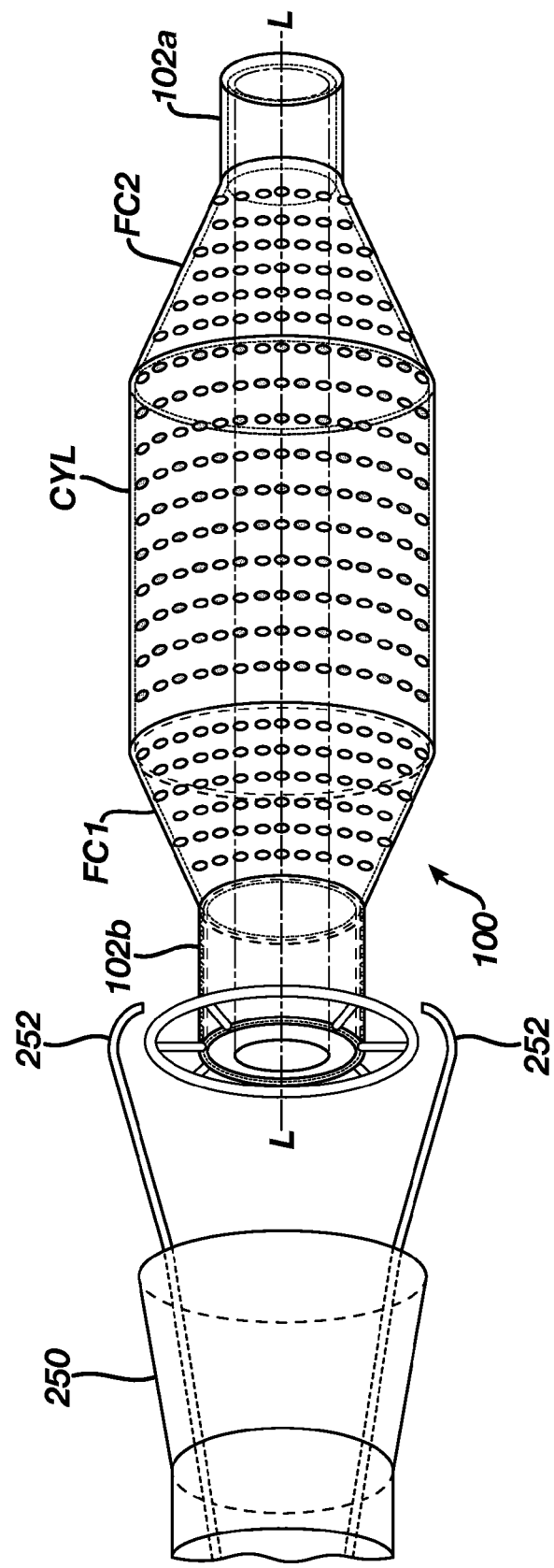
FIG. 2B illustrates a portion of the retrieval system to retrieve the device of FIG. 2A.

Because the outer thin-film structure is made of a shape memory thin-film material that is set to expand at body temperature, the outer thin-film structure starts to expand causing the inner structure 102 to expand also. Saline can be provided to the port 206 through the inflation port 120 to assist in expansion of the outer and inner structures. Blood can start to fill the device as shown diagrammatically in FIG. 1B. A portion of the blood volume can flow through the first frustoconic section FC1 and through the second frustoconic section FC2 while a portion can act as a carrier fluid to push or deliver some of the bio-active agents 114 into the vessel tissue. Thereafter, the delivery catheter can disconnect from the device and withdrawn from the body. After certain duration for implantation, the device can be retrieved by insertion of a retrieval catheter 250. The retrieval catheter 250 may have a snare claw 252 or snare 254 to positively connect to the device 100 and pulled into the catheter 250 funnel-like opening (FIGS. 2B and 2C).

The inner polymer structure of prosthetic 100 is preferably made from a suitable material such as, for example PTFE, ePTFE, Dacron, PET (polyester), Fluoro-polymers such as PTFE and FEP, spun PTFE, HDPE, polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof, coatings from polymer dispersions such as polyurethane dispersions (for example, BAYHDROL® fibrin, collagen and derivatives thereof, polysaccharides such as celluloses, starches, dextrans, alginates and derivatives, hyaluronic acid, squalene emulsions. Polyacrylic acid, available as HYDROPLUS® (Boston Scientific Corporation, Natick, Mass.), and described in U.S. Pat. No. 5,091,205, the disclosure of which is hereby incorporated herein by reference, is particularly desirable. Even more desirable is a copolymer of polylactic acid and polycaprolactone. Suitable coverings include nylon, collagen, PTFE and expanded PTFE, polyethylene terephthalate and KEVLAR®, ultra-high molecular weight polyethylene, or any of the materials disclosed in U.S. Pat. No. 5,824,046 and U.S. Pat. No. 5,755,770, which are incorporated by reference herein. More generally, the material for the inner polymer structure layer may be synthetic polymers such as polyethylene, polypropylene, polyurethane, polyglycolic acid, polyesters, polyamides, their mixtures, blends and copolymers.

Alternatively, the inner polymer structure can be formed from biodegradable polymers such as polylactic acid (i.e., PLA), polyglycolic acid (i.e., PGA), polydioxanone (i.e., PDS), polyhydroxybutyrate (i.e., PHB), polyhydroxyvalerate (i.e., PHV), and copolymers or a combination of PHB and PHV (available commercially as Biopol®), polycaprolactone (available as Capronor®), polyanhydrides (aliphatic polyanhydrides in the back bone or side chains or aromatic polyanhydrides with benzene in the side chain), polyorthoesters, polyaminoacids (e.g., poly-L-lysine, polyglutamic acid), pseudo- polyaminoacids (e.g., with back bone of polyaminoacids altered), polycyanocrylates, or polyphosphazenes. As used herein, the term "bio-resorbable" includes a suitable biocompatible material, mixture of materials or partial components of materials being degraded into other generally non-toxic materials by an agent present in biological tissue (i.e., being bio-degradable via a suitable mechanism, such as, for example, hydrolysis) or being removed by cellular activity (i.e., bioresorption, bioabsorption, or bioresorbable), by bulk or surface degradation (i.e., bioerosion such as, for example, by utilizing a water insoluble polymer that is soluble in water upon contact with biological tissue or fluid), or a combination of one or more of the bio-degradable, bio-erodable, or bio-resorbable material noted above.

The bio-active agents may also be used to load into the pores or blended into the inner polymer structure. Such agents may include one or more non-genetic therapeutic agents, genetic materials and cells and combinations thereof as well as other polymeric coatings. Non-genetic therapeutic agents include anti-thrombogenic agents such as heparin, heparin derivatives, urokinase, and PPack (dextrophenylalanine proline arginine chloromethylketone); antiproliferative agents such as enoxaprin, angiopeptin, or monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine, and ropivacaine; anti-coagulants, an RGD peptide-containing compound, heparin, antithrombin compounds, platelet receptor antagonists, anti-thrombin anticodies, anti-platelet receptor antibodies, aspirin, prostaglandin inhibitors, platelet inhibitors and tick antiplatelet peptides; vascular cell growth promotors such as growth factor inhibitors, growth factor receptor antagonists, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; and agents which interfere with endogenous vasoactive mechanisms.

Genetic materials include anti-sense DNA and RNA, DNA coding for, anti-sense RNA, tRNA or rRNA to replace defective or deficient endogenous molecules, angiogenic factors including growth factors such as acidic and basic fibroblast growth factors, vascular endothelial growth factor, epidermal growth factor, transforming growth factor alpha and beta, platelet-derived endothelial growth factor, platelet-derived growth factor, tumor necrosis factor alpha, hepatocyte growth factor and insulin like growth factor, cell cycle inhibitors including CD inhibitors, thymidine kinase ("TK") and other agents useful for interfering with cell proliferation the family of bone morphogenic proteins ("BMPs"), BMP-2, BMP-3, BMP-4, BMP-5, BMP-6 (Vgr-1), BMP-7 (OP-I), BMP-8, BMP-9, BMP-IO, BMP-I, BMP-12, BMP-13, BMP-14, BMP-15, and BMP-16. Desirable BMPs are any of BMP-2, BMP-3, BMP-4, BMP-5,BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA encoding them.

Cells can be of human origin (autologous or allogeneic) or from an animal source (xenogeneic), genetically engineered if desired to deliver proteins of interest at the deployment site. The cells may be provided in a delivery media. The delivery media may be formulated as needed to maintain cell function and viability.

It is noted that the utilization of the outer thin-film structure with a thin-film shape memory material and an inner polymer structure, as shown and described (with some of the particular features for some embodiments and all of the features for other embodiments), allows for the following key benefits: (a) the thin-film outer structure by virtue of its metallic material, has greater lubricity; (b) the thin-film material is interposed between the body vessel tissue so as to mitigate or reduce an inflammatory response if the polymer layer were to contact the body vessel tissue directly; (c) the polymer layer discourages excessive tissue ingrowth, thereby allowing the device to be retrieved without excessive trauma to the surrounding tissues; (d) the pores allow for continued blood flow through the composite device, albeit at a lower flow rate; (e) the construction of the composite device allows for insertion of the delivery catheter to allow for delivery of new drugs or bio-active agents other than the bio-active agents that were originally loaded into the pores or blended into the polymer materials at the initial implantation of the device; and (f) the thin-film outer structure is believed to prevent delamination of the inner polymer structure thereby reducing local toxicity or inflammatory response of the patient.

While the invention has been described in terms of particular variations and illustrative figures, those of ordinary skill in the art will recognize that the invention is not limited to the variations or figures described. In addition, where methods and steps described above indicate certain events occurring in certain order, it is intended that certain steps do not have to be performed in the order described but in any order as long as the steps allow the embodiments to function for their intended purposes. Therefore, to the extent there are variations of the invention, which are within the spirit of the disclosure or equivalent to the inventions found in the claims, it is the intent that this patent will cover those variations as well.

What is claimed is:

1. An endovascular prosthesis comprising:
   an inner polymer structure that extends from a distal end to a proximal end along a longitudinal axis, the inner polymer structure having an inner surface facing the longitudinal axis with a first plurality of pores with each pore extending from the inner surface to an outer surface of the polymer structure; and
   an outer thin-film shape-memory structure having an inner thin-film surface coupled to the outer surface of the inner polymer structure from the distal end to the proximal end with a retrieval member at the proximal end to allow for the prosthesis to be retrieved after placement in a body vessel, the outer thin-film shape-memory structure configured with a second plurality of pores with each pore extending from the inner thin-film surface to an outer thin-film surface so that fluid communication is provided from inside of the inner polymer structure to the body vessel.

2. The endovascular prosthesis of claim 1, in which one of the first and second pluralities of pores includes a proportion of the pores filled with a bio-active material for elution directly into the body vessel.

3. The endovascular prosthesis of claim 2, in which the proportion of pores with bio-active materials includes 80% of the plurality of pores.

4. The endovascular prosthesis of claim 1, in which the inner polymer structure is connected to a guidewire lumen that extends through the proximal end to the distal end to allow for insertion of a guide wire.

5. The endovascular prosthesis of claim 4, in which the guidewire lumen is disposed between the inner polymer structure and an inflation lumen.

6. The endovascular prosthesis of claim 5, in which the inner polymer structure includes a polyethylene material.

7. The endovascular prosthesis of claim 5, in which the inner polymer structure includes a polymer blended with bio-active agents configured to timed release of the agents.

8. The endovascular prosthesis of claim 5, in which the inner polymer structure includes a biodegradable polymer.

9. The endovascular prosthesis of claim 5, in which the outer thin-film shape-memory structure includes a biocompatible metal.

10. The endovascular prosthesis of claim 9, in which biocompatible metal includes a thin-film of nitinol.

11. The endovascular prosthesis of claim 9, in which biocompatible metal includes a thin-film of cobalt chromium.

12. The endovascular prosthesis of claim 1, in which the outer thin-film structure includes a first frustoconic joining a cylinder and terminating in a second frustoconic to define the overall outer shape of the prosthesis.

13. The endovascular prosthesis of claim 12, in which at least one of the first and second pluralities of pores is disposed in a radial direction with respect to the longitudinal axis.

14. The endovascular prosthesis of claim 13, in which at least one of the first and second pluralities of pores disposed on the first and second frustoconic allows for a portion of blood in the body vessel to flow through the pores on the first and second frustoconic.

15. The endovascular prosthesis of claim 14, in which the retrieval member includes a hook configured to engage with a retrieval snare of a retrieval catheter.

16. The endovascular prosthesis of claim 14, in which the retrieval member includes a radial member configured to engage with retrieval claws of a retrieval catheter.

17. The endovascular prosthesis of claim 1, in which the first plurality of pores of the inner polymer structure are aligned with respective second plurality of pores of the thin-film outer thin-film structure.

18. A method of introducing an endovascular prosthetic into a blood vessel of a patient, the method comprising the steps of:
   providing the prosthetic having:
      an inner polymer structure that extends from a distal end to a proximal end along a longitudinal axis, the inner polymer structure having an inner surface facing the longitudinal axis with a first plurality of pores with each pore extending from the inner surface to an outer surface of the polymer structure; and
      an outer thin-film shape-memory structure having an inner thin-film surface coupled to the outer surface of the inner polymer structure from the distal end to the proximal end with a retrieval member at the proximal end to allow for the prosthetic to be retrieved after placement in a body vessel, the outer thin-film shape-memory structure configured with a second plurality of pores with each pore extending from the inner thin-film surface to an outer thin-film surface so that fluid communication is provided from inside of the inner polymer structure to the body vessel;

inserting the prosthetic mounted on a delivery catheter into a blood vessel proximate a location with arterial deposits on an inner wall of the blood vessel;

deploying the prosthetic in the blood vessel proximate the location with arterial deposits;

removing the delivery catheter from the blood vessel; and retrieving the prosthetic after a time period subsequent to the deploying step.

* * * * *